(12) United States Patent
Yardibi et al.

(10) Patent No.: US 11,666,304 B2
(45) Date of Patent: Jun. 6, 2023

(54) PORTABLE ULTRASOUND BASED NERVE IMAGING SYSTEM

(71) Applicant: Medos International Sarl, Le Locle (CH)

(72) Inventors: Tarik Yardibi, Wayland, MA (US); Richard Patrick Courtis, Dorchester, MA (US); Emir Osmanagic, Norwell, MA (US); Leonard Bryant Guffey, Duxbury, MA (US); Christopher Robert Wagner, Welwyn Garden City (GB); Joshua John Gibson, London (GB); Alireza Mashal, Middleton, WI (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 473 days.

(21) Appl. No.: 16/277,902

(22) Filed: Feb. 15, 2019

(65) Prior Publication Data

US 2020/0261051 A1 Aug. 20, 2020

(51) Int. Cl.
*A61B 8/08* (2006.01)
*A61B 34/20* (2016.01)
(Continued)

(52) U.S. Cl.
CPC ............... *A61B 8/085* (2013.01); *A61B 8/12* (2013.01); *A61B 8/4427* (2013.01); *A61B 34/20* (2016.02);
(Continued)

(58) Field of Classification Search
CPC ...... A61B 2034/2065; A61B 2034/301; A61B 2090/365; A61B 2090/367;
(Continued)

(56) References Cited

U.S. PATENT DOCUMENTS

2009/0326363 A1* 12/2009 Li .................. A61B 8/483
600/411
2011/0098572 A1* 4/2011 Chen .................. A61B 5/0062
600/463
(Continued)

FOREIGN PATENT DOCUMENTS

WO 2015159296 A1 10/2015

OTHER PUBLICATIONS

Hafiane et al. "Deep Learning with Spatiotemporal Consistency for Nerve Segmentation in Ultrasound Images." arXiv:1706.05870. Jun. 19, 2017. (Year: 2017).*
(Continued)

*Primary Examiner* — Amelie R Davis
(74) *Attorney, Agent, or Firm* — Barnes & Thornburg, LLP

(57) ABSTRACT

An ultrasound probe for percutaneous insertion into an incision and related methods are disclosed herein, e.g., for imaging neural structures at a surgical site of a patient. An exemplary ultrasound probe can be a portable ultrasound probe configured to be passed percutaneously into an incision and can have an imaging region extending distally from a distal tip of the probe. In one embodiment the ultrasound probe can be a navigated portable ultrasound probe. The ultrasound probe can be connected to a computing station and configured to transmit images to the computing station for processing. In another embodiment, an ultrasound probe can be part of a network of sensors, including at least one external sensor, where the network of sensors is configured to transmit images to the computing station for processing. The computing station can process and display images to visualize and/or highlight neurological structures in an imaged region.

14 Claims, 8 Drawing Sheets

(51) Int. Cl.
*G16H 50/20* (2018.01)
*A61B 8/12* (2006.01)
*A61B 8/00* (2006.01)
*G06T 7/10* (2017.01)
*G06T 7/00* (2017.01)
*A61B 34/30* (2016.01)
*A61B 90/00* (2016.01)

(52) U.S. Cl.
CPC .............. *G06T 7/0012* (2013.01); *G06T 7/10* (2017.01); *G16H 50/20* (2018.01); *A61B 2034/2065* (2016.02); *A61B 2034/301* (2016.02); *A61B 2090/365* (2016.02); *A61B 2090/367* (2016.02); *A61B 2090/3784* (2016.02); *G06T 2207/10132* (2013.01); *G06T 2207/20081* (2013.01); *G06T 2207/30012* (2013.01)

(58) Field of Classification Search
CPC ............ A61B 2090/3784; A61B 34/20; A61B 5/0066; A61B 5/389; A61B 5/4893; A61B 8/085; A61B 8/12; A61B 8/4218; A61B 8/4254; A61B 8/4263; A61B 8/4416; A61B 8/4427; A61B 8/4472; A61B 8/4477; A61B 8/5207; G16H 50/20; G06T 2207/20081; G06T 7/0012; G06T 7/10; G06T 2207/30012
See application file for complete search history.

(56) References Cited

U.S. PATENT DOCUMENTS

| | | |
|---|---|---|
| 2011/0118603 A1 | 5/2011 | Suh et al. |
| 2011/0152684 A1* | 6/2011 | Altmann .................. A61B 8/12 600/443 |
| 2012/0123292 A1* | 5/2012 | Fagin .................. A61B 5/4893 600/554 |
| 2013/0324989 A1 | 12/2013 | Leung et al. |
| 2014/0051999 A1 | 2/2014 | Gharib et al. |
| 2017/0156691 A1* | 6/2017 | Cabrera-Munoz ....... A61B 8/12 |
| 2019/0192116 A1* | 6/2019 | Beckers ............... C09D 109/00 |
| 2020/0146717 A1* | 5/2020 | Krause .................. A61B 90/10 |

OTHER PUBLICATIONS

International Search Report and Written Opinion for application PCT/IB2020/051265 dated May 15, 2020 (15 Pages).

* cited by examiner

PORTABLE ULTRASOUND BASED NERVE IMAGING SYSTEM

FIELD

The present disclosure is related to systems and methods for identifying neural structures present at a surgical site.

BACKGROUND

Perioperative neurological injury is a known complication associated with elective spinal surgery that has become a more common occurrence in recent years. Contacting neurological structures during a surgical procedure can result in neurological injury and complications. Some examples of perioperative neurological complications that may result from spinal surgery include vascular injury, durotomy, nerve root injury, and direct mechanical compression of the spinal cord or nerve roots during vertebral column instrumentation. Such neurological complications are associated with longer hospital stays, higher total charges, and increased in-hospital mortality.

While minimally invasive spine surgery (MISS) has many known benefits, there is a significantly higher rate of neurological complications associated with MISS procedures than traditional open surgical techniques. MISS procedures, accessing the spine or a target surgical region often involves navigating a surgical instrument through patient anatomy including muscles, fatty tissue, and neurological structures. Current intra-operative imaging devices do not adequately show neurological structures in an operating region. For example, computed tomography (CT) and cone beam computed tomography (CBCT) imaging technology is often favored for intra-operative use to visualize musculoskeletal structures in an operating region of a patient's anatomy. CT and CBCT images, however, do not show neurological structures. While MRI imaging shows both musculoskeletal and neurological structures of a scanned patient anatomy, MRI imaging is typically used only to diagnose a patient and not for pre-operative surgical planning or intra-operative use. Moreover, ultrasound imaging cannot currently be used to effectively locate and assess neural structures at a surgical site. Due to the size of currently available ultrasound probes, a patient's spinal region must be scanned from outside the body cavity. As a result, ultrasound probes cannot be used to image nerves around the spine because neural structures cannot be seen through the skin. Furthermore, accurately predicting a location of neurological structures at a surgical site can be difficult due to wide variation in patient anatomy.

In surgical procedures today, technologies available for assessing nerve structures in the spine rely on multiple needle electrodes in a patient's arms or legs to locate motor nerves in the cervical and lumbar spine region and generate signals. This technology can be problematic due to anesthesia effects, electrical interference, or signal interpretation challenges. These systems typically require a neuro-monitoring specialist to interpret signals and guide a surgeon performing an operation.

Accordingly, there is a need for improved devices, systems, and methods to improve identification and assessment of neural structures at a surgical site.

SUMMARY

The present invention generally provides devices and methods for identifying and assessing neural structures at a surgical site. In some embodiments, a portable ultrasound probe is provided that can be inserted percutaneously through an incision in a patient to a surgical site to identify neurological structures. The portable ultrasound probe can be a forward-looking probe, having a small volume, high resolution imaging area. The probe can be a navigated ultrasound probe with a tracking element, where the navigated ultrasound probe forms a part of a surgical navigation system. Alternatively, the probe can be used as a stand-alone device. In some embodiments, the probe can include an imager in a distal tip of the probe. Additionally, or alternatively, the probe can include one or more sensors for optical and/or electrical nerve detection. In some embodiments, a method of identifying neural structures of the patient is provided that can include inserting a portable ultrasound probe through an incision at a surgical site, generating ultrasonic data using the probe, and analyzing the data to identify neural structures at the surgical site. In some embodiments, the probe can communicate ultrasonic data to a computing station for further processing and analysis. In other embodiments, a network of sensors, including the probe and at least one sensor located externally with respect to the patient, can be configured to generate ultrasonic data and transmit the data to a computing station. The computing station can create and process images from the received data, and can communicate information to a user. While the systems, devices, and methods described herein can be utilized in a variety of surgical procedures, they can have particular utility in various orthopedic or neurologic surgical procedures, such as spinal operations and, in particular, minimally invasive spinal procedures.

In one aspect, a method of identifying neural structures of a patient is provided that can include inserting a portable ultrasonic probe percutaneously through an incision in the patient at a surgical site, generating ultrasonic data using the probe, and analyzing the data to identify neural structures at the surgical site.

The devices and methods described herein can have a number of additional features and/or variations, all of which are within the scope of the present disclosure. In some embodiments, for example, generating ultrasonic data can include collecting ultrasonic data from the probe. Further, in some embodiments, generating ultrasonic data can include a real-time collection of ultrasonic data from the probe while the probe is percutaneously inserted through the incision. In some embodiments, generating ultrasonic data can include collecting data from one or more ultrasonic sensor located external to the patient and directed toward an area containing the probe.

In some embodiments, analyzing the data to identify neural structures at the surgical site can include processing ultrasonic data using a deep learning algorithm to automatically identify at least one neural structure.

In some embodiments, the method can further include transmitting data from the probe to a computing station and communicating information about at least one identified neural structure near a tip of the probe to a user. In certain embodiments, the method can further include creating a two-dimensional or a three-dimensional map of the at least one identified neural structure.

In some embodiments inserting the probe can include manually inserting the probe through the incision. In other embodiments, inserting the probe through the incision can include robotically assisted navigation of the probe. The method can also include passing the probe through an access port at the incision.

In some embodiments, the probe can be a forward looking probe. Further, in some embodiments, the probe can have a focused forward range of about 1 inch or less. In certain embodiments the probe can have a diameter of 10 mm or less. Still further, in some embodiments the probe can include at least one optical or electrical nerve detection technologies.

In some embodiments, the method can further include registering images produced by the probe to a segmented anatomical structure of a patient image volume.

In another aspect, a system for detecting nerves is provided that can include a portable ultrasonic probe configured to be passed percutaneously through an incision to a surgical area in a patient, and a computing station configured to receive ultrasonic data and process the data to detect at least one neural structure in the surgical area.

In some embodiments, the computing station can further include a processor having a deep learning segmentation algorithm configured to automatically identify and localize neural structures in the surgical area from the ultrasonic data.

In some embodiments, the computing station can be configured to display a visual representation of at least one detected neural structure.

In some embodiments, the computing station can be a computer assisted navigation environment.

The probe can have a variety of configurations. For example, in some embodiments the probe can have a focused forward range of about 1 inch or less. In some embodiments, the probe can have a diameter of about 10 mm or less. Further, in some embodiments, the probe can be configured to be passed through an access port at the incision.

In some embodiments, the computing station can be configured to receive ultrasonic data from the probe.

In some embodiments, the system can further include a network of sensors including the probe and at least one ultrasonic sensor located externally with respect to the patient, where the network of sensors can be configured to transmit ultrasonic data to the computing station.

Any of the features or variations described above can be applied to any particular aspect or embodiment of the present disclosure in a number of different combinations. The absence of explicit recitation of any particular combination is due solely to the avoidance of repetition in this summary.

BRIEF DESCRIPTION OF THE DRAWINGS

The aspects and embodiments of the invention described above will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure.

Additionally, to the extent that linear or circular dimensions are used in the description of the disclosed devices and methods, such dimensions are not intended to limit the types of shapes that can be used in conjunction with such devices and methods. A person skilled in the art will recognize that an equivalent to such linear and circular dimensions can easily be determined for any geometric shape. Still further, sizes and shapes of the devices, and the components thereof, can depend at least on the anatomy of the subject in which the devices will be used, the size and shape of components with which the devices will be used, and the methods and procedures in which the devices will be used.

While the illustrated embodiments and accompanying description make particular reference to application in a spinal surgery procedure, and, in particular, to minimally invasive spinal surgery, the devices, systems, and methods described herein are not limited to these applications.

The devices, systems, and methods of the present invention are generally directed to identifying and assessing neural structures located near a surgical region. A portable ultrasound probe can be inserted percutaneously through an incision in a patient to image neural structures of the patient's anatomy. The probe can be connected or attached to a computing station which can be configured to receive data from the probe and process or analyze the data to detect at least one neurological structure near a tip of the probe.

Figure 1:
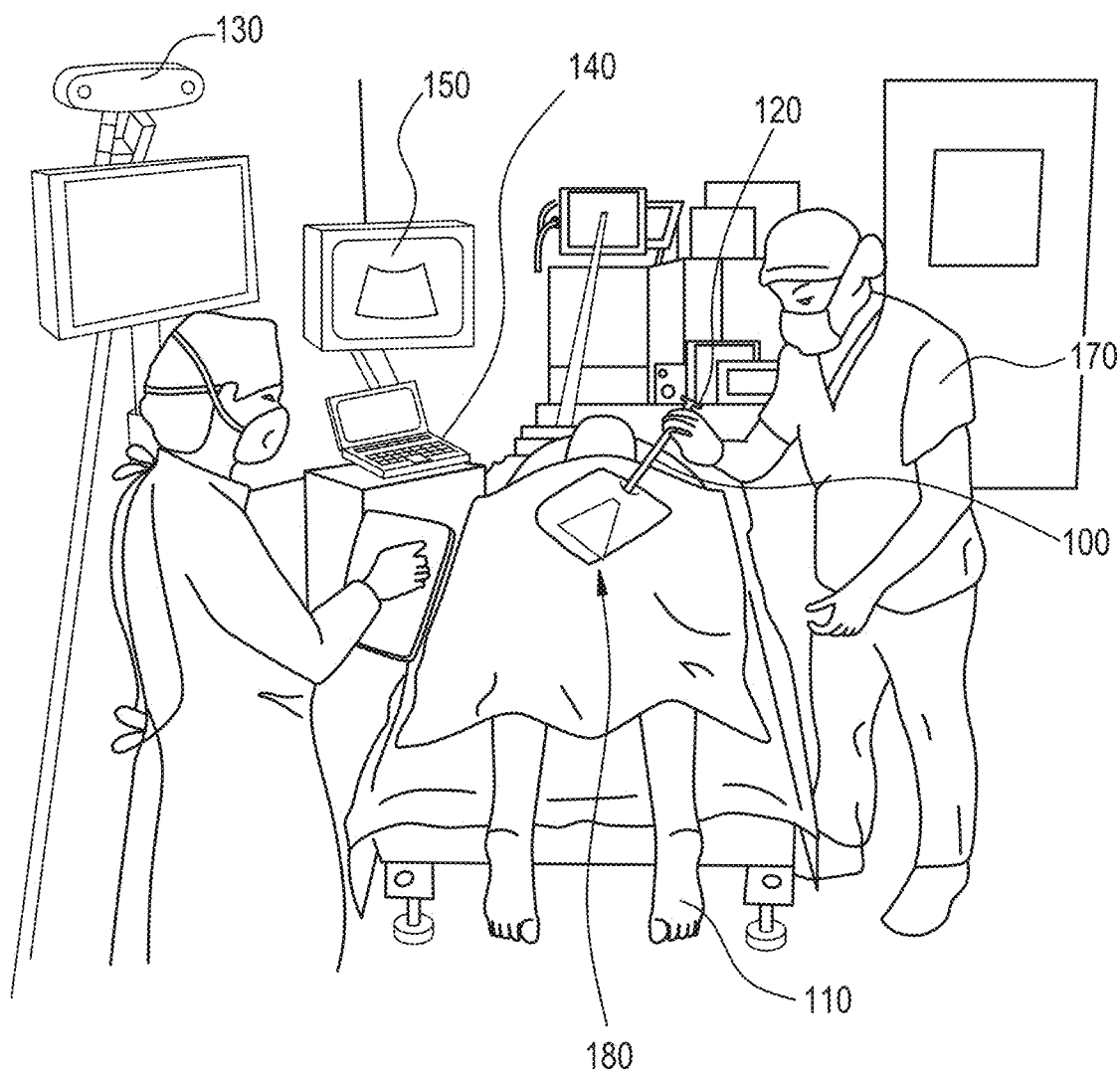
FIG. 1 illustrates an exemplary embodiment of a system of the present invention including a navigated ultrasound probe.

FIG. 1 illustrates an exemplary embodiment of a system of the present invention including a navigated ultrasound probe 100 inserted percutaneously through an incision in a patient 110. The probe 100 can have a reflective marker or tracking array 120 (or any other kind of tracking element, such as an inertial motion sensor, etc.) such that the probe 100 can be registered as part of a surgical navigation system. Any surgical navigation system known in the art can be used to achieve an accurate localization and virtual display of the probe 100. For example, the probe 100 can be coupled to an optical or an electromagnetic navigation system. In one embodiment, a stereotactic camera 130 can be mounted at the ceiling above an operating table. A computing station 140 with a display screen 150 can include navigation system software such that information can be transmitted to the computing station 140 from at least one component of a navigation system. As illustrated in FIG. 1, the probe 100 can be manually controlled by a surgeon or a user 170. Alternatively, the probe 100 can be held by a robotic device.

The probe 100 can be a forward looking probe having an imager in a distal tip of the probe that provides a small volume, high resolution focused imaging area 180. In one embodiment, the imager can comprise a capacitive micromachined ultrasonic transducer (CMUT) capacitive array. The imaging area 180 can preferably be a focused area extending in front of the tip of the probe to provide forward-looking images. In one embodiment, the probe can have a focused imaging area 180 extending about 25 mm in front of the probe. By way of further example, the imaging area 180 can extend in front of the probe between about 10 mm and 25 mm.

The tracking array 120 can be attached to a proximal end of the probe 100. The tracking array 120 can be used by a navigation system to accurately localize and image a position and motion of the probe relative to a patient 160. The tracking array 120 can have at least three reflective marker spheres such that a navigation system can accurately calculate a position and orientation of the attached probe 100. In one embodiment, the stereoscopic camera 130 can emit infrared light which can be received by the tracking array 120 and used to determine a position of the tracking array 120 in a three-dimensional space. As the tracking array 120 moves, the stereoscopic camera 130 can be used to provide real-time tracking of the tracking array's position. The location information can be transmitted to the computing station 140 and displayed on the display 150. It will be appreciated by one having ordinary skill in the art that any known surgical navigation system can be used to achieve an accurate localization and virtual display of the probe 100.

Figure 2:
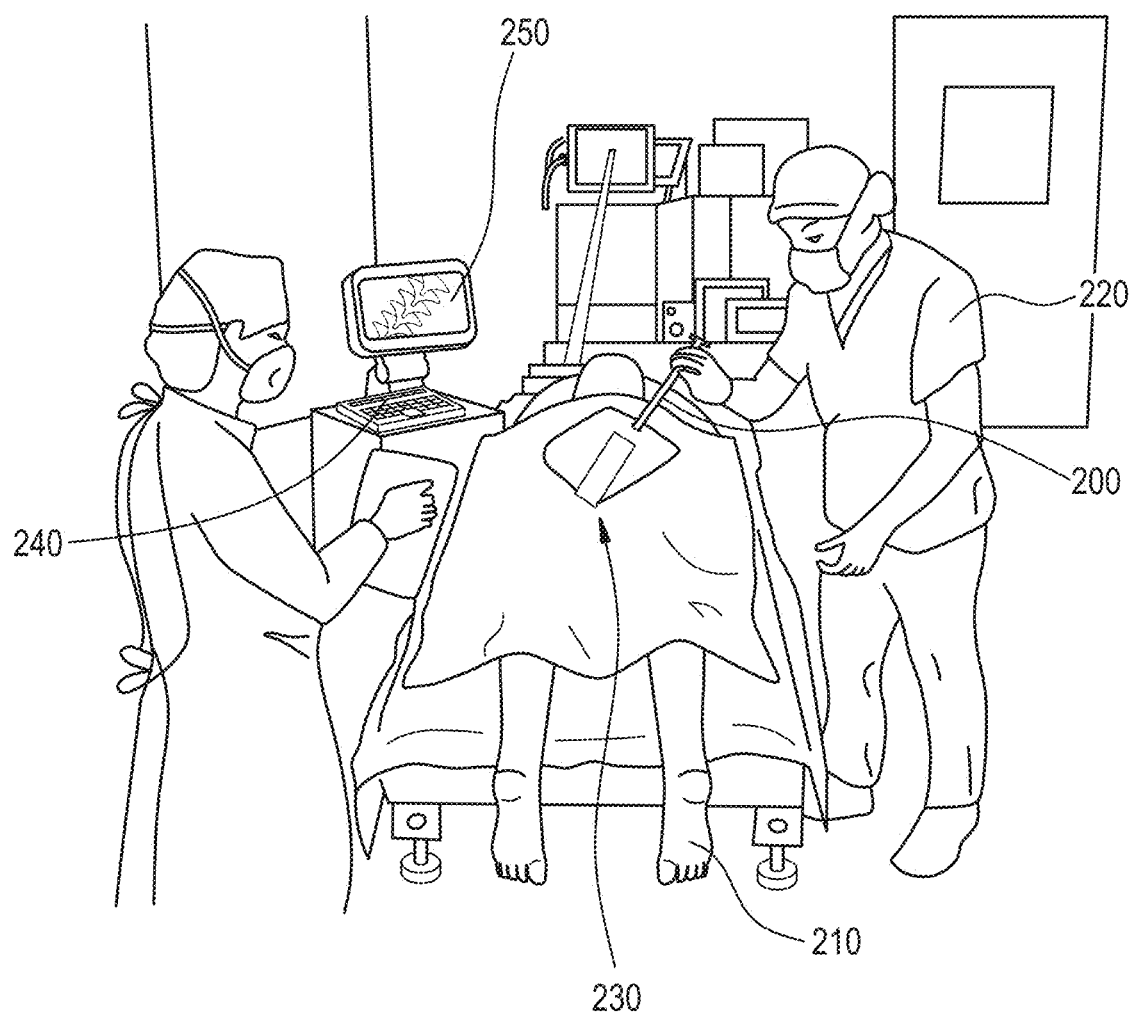
FIG. 2 illustrates another exemplary embodiment of a system of the present invention.

In an alternative exemplary embodiment of a system of the present invention, FIG. 2 shows a portable ultrasound device 200 inserted percutaneously through an incision in a patient 210 as a standalone device to provide rapid imaging and detection of neural structures. The probe 200 can be hand held and operated by a surgeon or a user 220. Alternatively, the probe 200 can be held and operated by a robotic device. In one embodiment, the probe 200 can include at least one sensor which can provide "look ahead" or forward looking information about possible presence of nerves in a sensing area 230. A sensor of the probe can include optical and/or electrical nerve detection technology. By way of non-limiting example, optical nerve detection technology can provide optical stimulation such as optical coherence tomography, diffuse reflectoscopy, spectroscopy, and/or NIR light technology. Additionally or alternatively, electrical nerve detection technology can include electrical stimulation such as, for example, electromyography or mechanomyography. The probe 200 can also include an imager, such as an ultrasound transducer as discussed above, to provide high resolution images in an imaging range. In this manner, the probe 200 can provide hybrid sensing of neural structures in an imaged region of the patient 210. The probe 200 can be coupled to a computing station 240 and can be configured to transmit acquired data to the computing station 240 for processing. The computing station 240 can be configured to receive and process data from the probe 200 and display data on a display 250.

Figure 3:
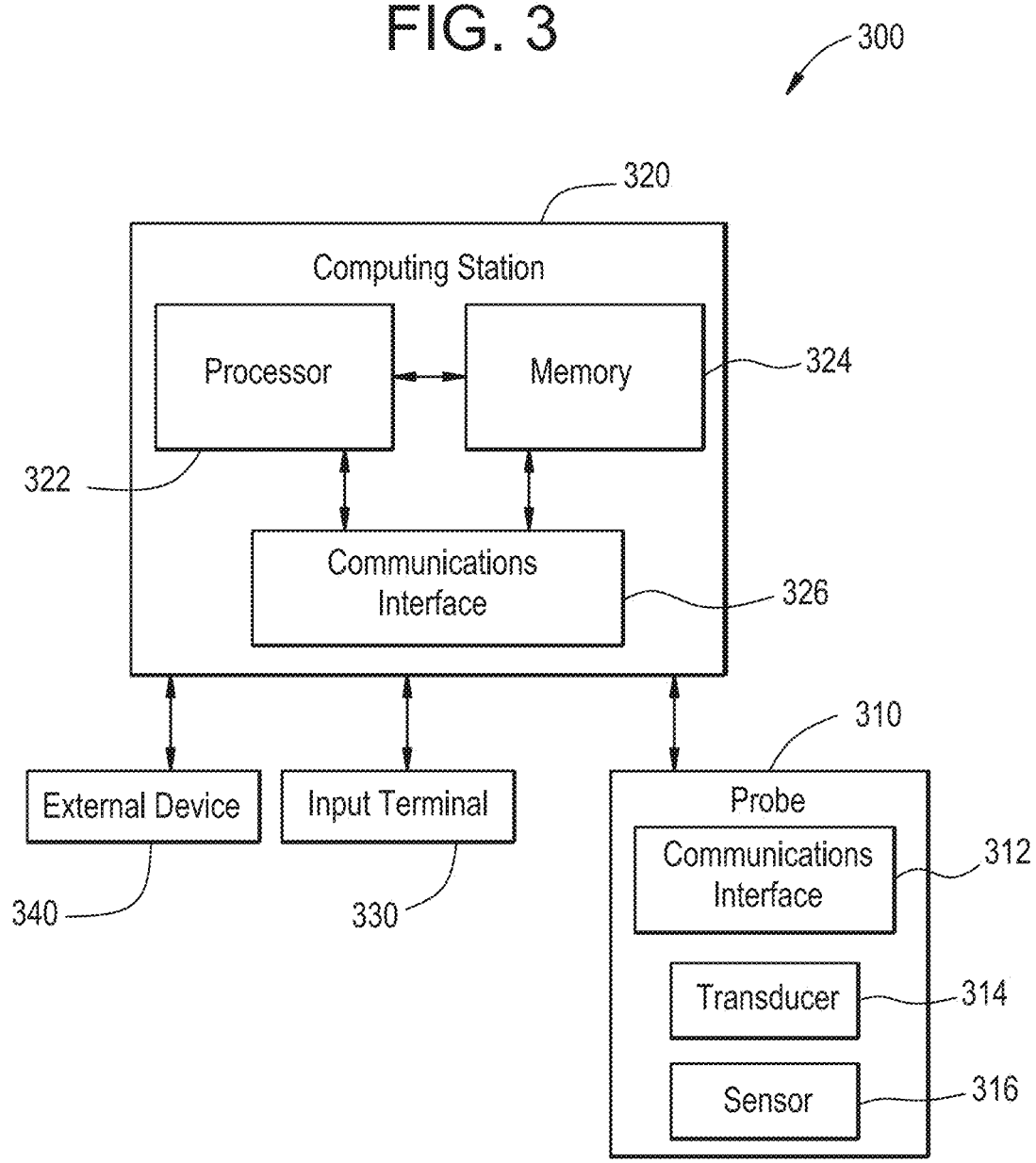
FIG. 3 schematically illustrates an exemplary system of the present invention.

FIG. 3 schematically illustrates an exemplary system 300 of the present invention. The system 300 can include an ultrasound probe 310, a computing station 320, an input terminal 330, and one or more external device 340. The computing station 320 can include a processor 322, a memory 324, and a communications interface 326, all of which can be in communication with each other. The communications interface 325 of the computing station 320 can be in communication with the probe 310, an input terminal 330, and an external device 340. The probe 310 can include a communications interface 312, a transducer 314, and a sensor 316—all of which can be in communication with each other. Although each of these components are referred to in the singular, it will be appreciated by a person skilled in the art that the various functions described as being carried out by one of the components can actually be carried out by multiple of these components, e.g., the functions described as being carried out by the processor 322 can be carried out by multiple processors.

The processor 322 can include a microcontroller, a microcomputer, a programmable logic controller (PLC), a field-programmable gate array (FPGA), an application specific integrated circuit (ASIC), integrated circuits generally referred to in the art as a computer, and other programmable circuits, and these terms are used interchangeably herein. The processor 322 can be configured to generate positional or identification information and/or perform various calculations based on, for example, data received from the probe 310, data stored in the memory 324, and/or received from an external device 340 or input terminal 330 via the communications interface 326. By way of non-limiting example, the processor 322 can be configured to process data received from an ultrasound probe 310 using known signal processing techniques, conventional image segmentation methods, and/or deep learning segmentation algorithms. The process 322 can be configured to process location information from a navigation system. The processor 322 can be configured to visualize a location of neurological structures and/or a location of an ultrasound probe 310.

The processor 322 can be coupled to the memory 324, which can include a random access memory (RAM), a read-only memory (ROM), a flash memory, a non-transitory computer readable storage medium, and so forth. The memory 324 can store instructions for execution by the processor 322 to implement the systems disclosed herein or to execute the methods disclosed herein. Additionally or alternatively, the memory 324 can store the information calculated by the processor 322 and/or received from an external device, an input terminal and/or a probe through the communications interface 326.

The probe 310 can be a portable ultrasound probe having a communications interface 312, a transducer 314, and at least one sensor 316. The communications interface 312 can be configured to receive and transmit information with any of the transducer 314, the sensor 316, and the communications interface 326 of the computing station 320. The communications interface 312 can be wireless (e.g., near-field communication (NFC), Wi-Fi, Bluetooth, Bluetooth LE, ZigBee, and the like) or wired (e.g., USB or Ethernet). The communication interface 312 can be selected to provide the desired communication range. In some embodiments, Bluetooth (e.g., class 2 Bluetooth having a range of 5-10 meters) can be used for the communication interface to allow the probe 310 to remain somewhat distant from the device with which it is communicating, e.g., the computing station 320, while at the same time limiting the communication range such that other mobile devices unlikely to be used in the surgery are not needlessly involved.

The ultrasound probe 310 can include a transducer 314 configured to send and receive ultrasonic sound waves. The transducer 314 can receive electrical currents from the computing station 320 to emit sound waves. An operator can control frequency, duration, and a scan mode of the ultrasound probe using transducer pulse controls in the computing station 320. The transducer can transmit data to the computing station 320 for processing.

The ultrasound probe 310 can include a sensor 316. In one embodiment, the sensor 316 can be or can include any type of sensor that is configured to detect or image neurological structures. By way of non-limiting example, the sensor 316 can include optical and/or electrical nerve detection technology. The sensor 316 can be configured as a single sensor or multiple sensors. The sensor 316 can include, for example, optical coherence tomography technology, diffuse reflectoscopy technology, spectroscopy technology, mechanomyography (MMG) technology, or electromyography (EMG) technology. The sensor 316 can be configured to detect or image neurological structures at intervals, for example every second, every millisecond, every microsecond, etc., such that neurological structure detection information is effectively detected continuously and in real-time. Detection can occur regularly, intermittently, or at non-regular intervals. Information detected by the sensor 316 can be communicated to the computing station 320 via the communications interface 312 for processing or storage.

The computing station 320 can also be connected to one or more external device 340 and one or more input terminal 330 via the communications interface 326. By way of non-limiting example, the external device 340 can be a display, a navigation system, a computing device, and/or a surgical instrument or sensor. An input terminal 330 can be configured to allow a surgeon or other user to input data directly into the computing station 320. Input data can include patient information, surgical procedure information, and the like. The input terminal 330 can be any known input device, for example, a keyboard and/or a cursor.

Figure 4:
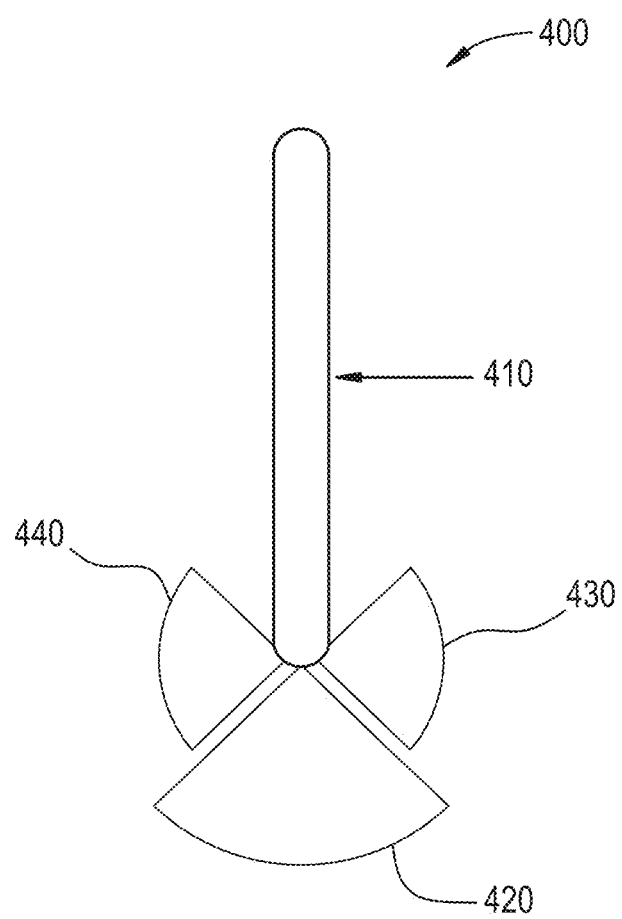
FIG. 4 shows an exemplary embodiment of an ultrasound probe of the present invention.

FIG. 4 shows an exemplary embodiment of a probe 400. The probe 400 can be a portable ultrasound probe that provides rapid imaging and detection of neural structures in an imaging region. The probe 400 can be configured for percutaneous insertion through an incision at a surgical site. In one embodiment, the probe 400 can be configured for use in a minimally invasive surgical procedure. A probe body 410 can have a diameter small enough to fit through an access port to a surgical site. By way of non-limiting example, the probe body 410 can have a diameter of about 10 mm or less. In one embodiment, the probe body 410 can have a diameter of about 6 mm or less.

The probe 400 can have a forward looking primary imaging area 420. The primary imaging area 420 can represent a region in which the probe 400 can image neural structures. For example, when the probe 400 is percutaneously inserted through an incision in a spinal region of a patient, the probe 400 can detect neural structures—e.g., nerve roots, spinal cord, and cauda equina—in the primary imaging area 420. As discussed above, the primary imaging area can have a focused range of about 25 mm or less. In an embodiment of a probe 410 that includes additional sensing technologies, such as optical and/or electrical stimulation, a sensing range can either align or extend beyond the primary imaging area 420. A sensing range can be a function of selected additional sensing technologies, as is known in the art.

Additionally, the probe 400 can have at least one secondary imaging area 430 extending laterally from the probe body 410. In one embodiment, the secondary imaging area can be greater than or equal to about 6 mm. In one embodiment, the probe can have multiple secondary imaging areas 430, 440 extending from multiple sides of the probe body 410. The probe 400 can include any known imaging or sensing technology.

Figure 5:
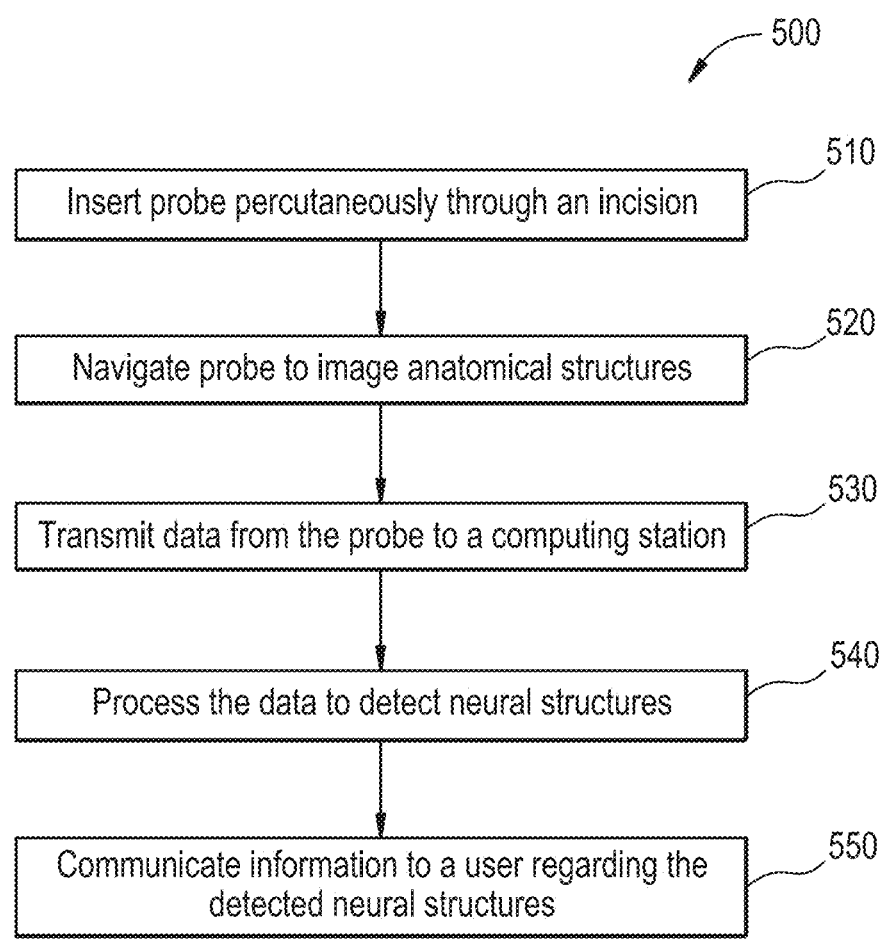
FIG. 5 illustrates an exemplary method of the present invention of identifying neural structures using an ultrasound probe.

FIG. 5 shows an exemplary method 500 of using a probe of the present invention to identify and image neural structures in an imaging region. The probe can be used both pre-operatively, for example to plan incisions or placement of pedicle screw or as guidance for pre-operative navigation, and/or intra-operatively, for example to take detailed plans and align with an intra-operative reference frame. In one embodiment, the systems, methods, and devices disclosed herein can be used in a minimally invasive spinal surgery access procedure to image exiting nerve roots, transverse processes, and/or the spinal cord. By way of non-limiting example, such procedures can include a transforaminal approach or a lateral approach, requiring navigation through psoas muscles.

A first step (510) can include inserting a portable ultrasound probe percutaneously through an incision at a surgical site of a patient. In one embodiment, a probe can be percutaneously inserted through an access port or tube placed at an incision site. The probe can be inserted either manually by a human or can be inserted or assisted by a robotic device. The probe can be inserted such that at least an imaging portion of the probe passes percutaneously through the incision into a body cavity of the patient.

Once inserted, the probe can be navigated for collecting images of anatomical structures in an imaging region (520). In one embodiment, the probe can be a forward looking probe having an imaging area extending distally from a distal tip of the probe. In another exemplary embodiment, the probe can have at least one additional imaging area extending laterally from a body of the probe. In yet another exemplary embodiment, the probe can have additional sensors to provide hybrid sensing of neural structures. The additional sensors can be located at the tip of the probe and/or along the body of the probe.

The probe can then transmit raw data to a connected computing station (530). Any known method of data transfer between the probe and a computing station can be used. The connection and data transfer between the probe and the computing station can be wireless (e.g., near-field communication (NFC), Wi-Fi, Bluetooth LE, and the like) or wired (e.g., USB or Ethernet). In one embodiment, the probe can transmit raw data to the computing station in real time.

The computing station can then process raw data to detect neural structures (540). The computing station can analyze the ultrasonic images collected from the probe using pattern recognition or other analytical techniques. In one embodiment, the computing station can receive raw data from the ultrasound probe and can create nerve images using beamforming or other signal processing techniques known in the art. The computing station can process images digitally to improve contrast and/or tune the image for optimal resolution by adjusting various gains in the probe hardware. For example, the computing system can apply a time gain compensation to account for tissue attenuation in the ultrasound imaging. Any known processing methods can be applied to improve contrast, quality, and resolution of images generated from the ultrasound probe. In one embodiment, the computing station can use conventional image segmentation methods, as is known in the art, to process ultrasound images.

In another embodiment, the computing station can process images using deep-learning based semantic segmentation algorithms. Trained convolution neural networks or U-Nets can be used to automatically identify and localize neural structures, as well as bony landmarks, from the raw ultrasound probe data. Using deep-learning algorithms to identify neural structures can improve nerve imaging performance by leveraging anatomical knowledge. For example, nerve roots are expected to be close to transverse processes. In one embodiment, clinicians can train a U-Net to learn associations between a location of a neural structure, e.g., a nerve root and a location of bone, e.g., a transverse process. For example, clinicians can annotate training images, such as MRI images, to identify neurological structures as well as musculoskeletal structures. A deep-learning algorithm can build a model associating an expected location of neurological structures from a known location of musculoskeletal structures, such as a transverse process. Clinicians can then annotate ultrasound images to identify musculoskeletal structures while leaving neurological structures unlabeled. The trained deep-learning algorithm can use the association model to identify imaged neurological structures near the corresponding musculoskeletal structures.

Using landmark based registration, a probe of the present invention can be registered to transverse processes in a spinal surgical region. A trained deep-learning algorithm of the present invention can then predict and identify a location of neural structures near the transverse processes from the ultrasound image data. Registering the probe can help achieve a better understanding of patient anatomy in the surgical region. In one embodiment, the probe can be registered to patient landmark anatomy and the computing system can then utilize MRI segmented nerves or bony structures detected by a CT or CBCT scan to build a more complete or robust image of a surgical region in which probe-detected data can be aligned and overlaid with MRI and/or CT data.

After processing the raw data, the computing station can communicate information to a user regarding detected neural structures (550). By way of non-limiting example, the computing station can communicate with a display screen to show images relating to neurological structures in an imaged area. In one embodiment, the computing station can display a 2D or 3D map of nerves ahead of a tip of the probe. In another embodiment, the computing station can display a 2D or 3D map of nerves in both a forward and lateral space relative to the probe. Information from the probe can be received, processed, and displayed in real or near-real time. By way of further example and as noted above, the computing station can highlight and display imaged neural structures overlaid on a patient scan volume, for example a CT, CBCT, or an MRI scan, of a surgical region. In an embodiment including a navigated probe, the computing station can provide and display direct three-dimensional visualization in space of the probe relative to a patient. The computing station can communicate information to a user regarding detected neural structures through other known methods as well.

Figure 6:
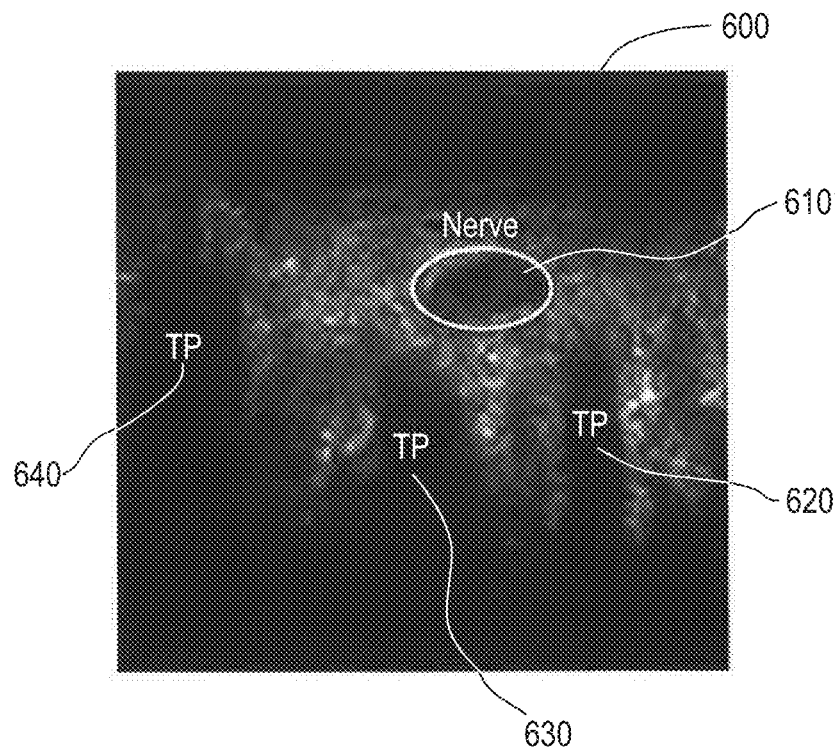
FIG. 6 shows an exemplary output of a system of the present invention identifying neural structures in an imaged region.
Figure 7:
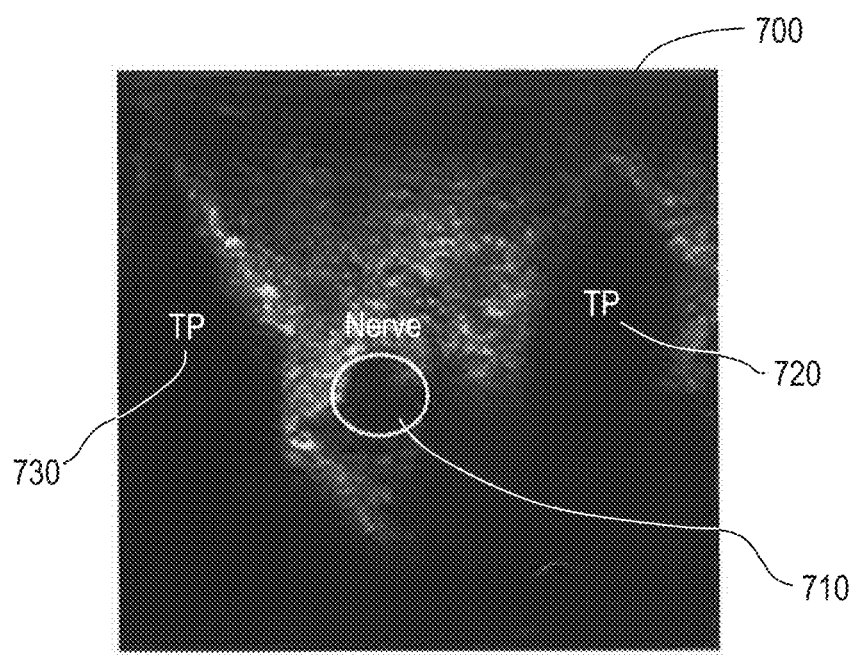
FIG. 7 shows another exemplary output of a system of the present invention identifying neural structures in an imaged region.
Figure 8:
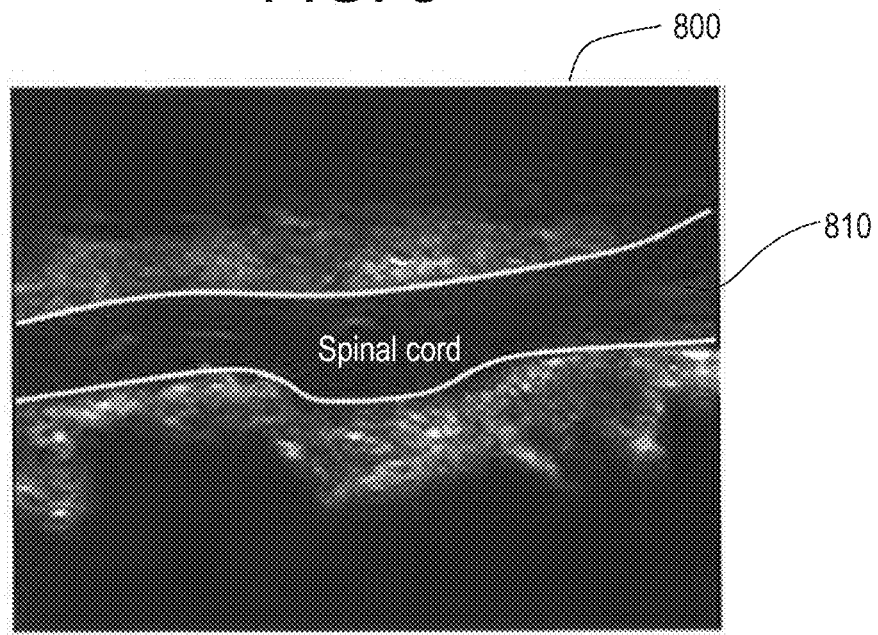
FIG. 8 shows another exemplary output of a system of the present invention identifying neural structures in an imaged region.
Figure 9:
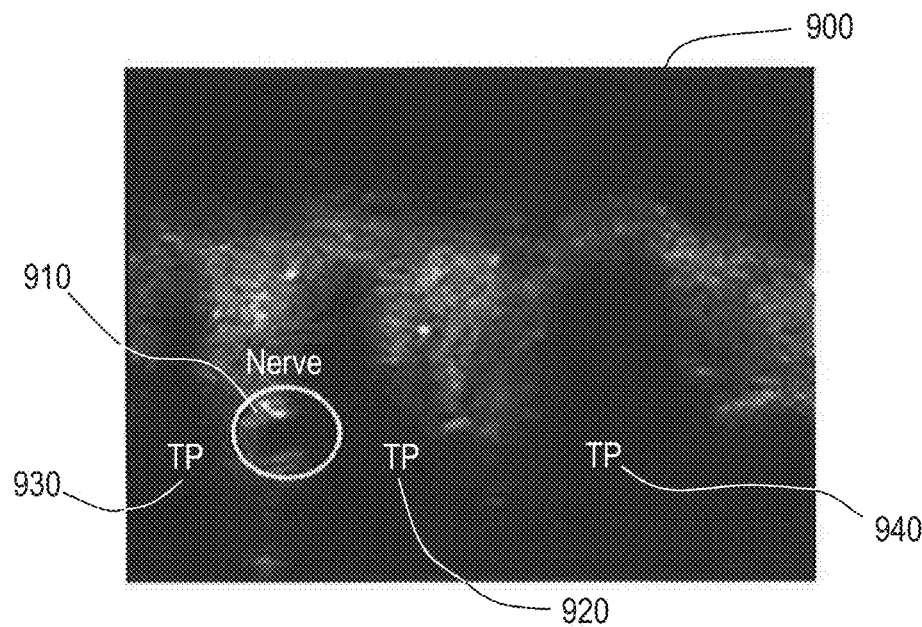
FIG. 9 shows another exemplary output of a system of the present invention identifying neural structures in an imaged region.

FIGS. 6-9 show exemplary images identifying neural structures imaged by an ultrasound probe of the present invention. In FIG. 6, an image 600 shows a nerve 610 and three transverse processes 620, 630, and 640. In FIG. 7, an image 700 shows a nerve 710 between two transverse processes 720 and 730. A spinal cord 810 is shown in an image 800 of FIG. 8. FIG. 9 shows an image 900 with a nerve 910 and three transverse processes 920, 930, and 940 identified. Each of the images 600, 700, 800, and 900 illustrate an image captured by an ultrasound probe of the present invention inserted percutaneously at an incision in a spinal region of a patient. The images 600, 700, 800, and 900 can be generated by a computing station after processing raw data received from the probe and can be displayed on a display that is coupled to the computing station for viewing by a surgeon or other person(s). Further, in some embodiments the identified nerves 610, 710, 910; transverse processes 620, 630, 640, 720, 730, 920, 930, 940; and spinal cord 810 can be identified as shown by a trained user, e.g., a surgeon. Such markings can then be utilized by, e.g., the above-noted deep-learning algorithms to learn patterns within the data that can allow the algorithm to identify such features without assistance. Once trained, systems according to the present disclosure employing a trained deep-learning architecture can create images having the identified markings of nerves 610, 710, 910; transverse processes 620, 630, 640, 720, 730, 920, 930, 940; and spinal cord 810 without user designation.

The above exemplary embodiments describe systems and methods where a portable ultrasound probe communicates with a computing station. In alternative embodiments, a portable ultrasound probe of the present invention can be part of a sensor network. In such embodiments, a computing station can communicate with the sensor network to receive ultrasonic data.

Figure 10:
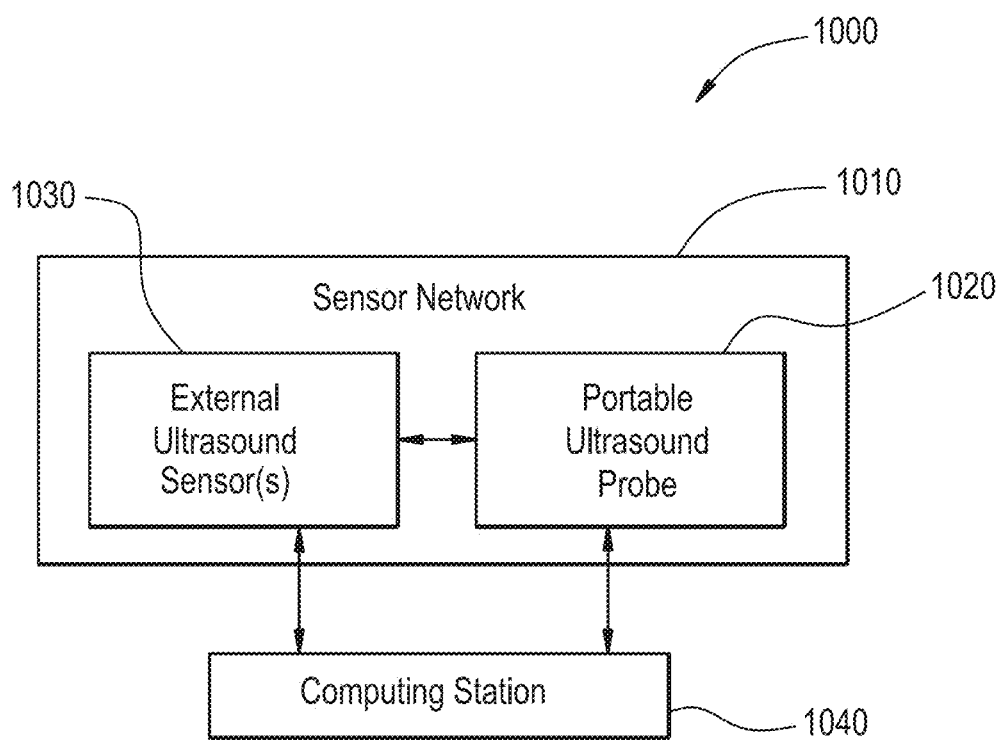
FIG. 10 schematically illustrates an alternative embodiment of a system of the present invention.

FIG. 10 illustrates an exemplary embodiment of a system 1000 of the present invention incorporating a sensor network 1010. For example, a sensor network 1010 can include a portable ultrasound probe 1020 configured for percutaneous insertion through an incision in a patient at a surgical site and at least one external ultrasound sensor 1030 that is located remote from the surgical site. The portable ultrasound probe 1020 and the at least one external ultrasound sensor 1030 can be in communication with each other to transmit and receive data. In one embodiment, an external ultrasound sensor can generate ultrasonic data using a portable ultrasound probe inserted percutaneously to a surgical site as a beacon to aid in signal processing of data collected by the external ultrasound sensor or sensors. In another embodiment, both an external ultrasound sensor (or sensors) and a portable ultrasound probe can generate ultrasonic data utilized to convey information to users. Incorporating at least one external ultrasound sensor can improve ultrasound images generated in association with the systems and methods described herein. It will be appreciated that any or all components of a sensor network 1010, i.e., a portable ultrasound probe 1020 and external ultrasound sensors 1030, can transmit data to a computing station 1040 for further data processing and analysis, as described above.

One skilled in the art will appreciate further features and advantages based on the above-described embodiments. Accordingly, the disclosure is not to be limited by what has been particularly shown and described. All publications and references cited herein are expressly incorporated herein by reference in their entirety.

The invention claimed is:

1. A method of identifying neural structures of a patient, the method comprising:
registering a portable ultrasonic probe with a surgical navigation system, the probe having a primary imaging area and at least one secondary imaging area, the primary imaging area being focused forward and the at least one secondary imaging area extending laterally from the probe;
inserting the probe percutaneously through an incision in the patient at a spinal surgical site;
identifying a location of the probe with the surgical navigation system;

registering the probe to a transverse process at the spinal surgical site;
generating ultrasonic data using the probe; and
analyzing the data to identify neural structures at the spinal surgical site;
wherein analyzing the data to identify neural structures includes predicting a location of at least one neural structure based on its anatomical location relative to the transverse process to which the probe is registered.

2. The method of claim 1, wherein generating ultrasonic data further comprises collecting ultrasonic data from the probe.

3. The method of claim 1, wherein generating the ultrasonic data further comprises a real-time collection of ultrasonic data while the probe is percutaneously inserted through the incision.

4. The method of claim 1, wherein generating the ultrasonic data further comprises collecting data from at least one ultrasonic sensor located external to the patient and directed toward an area containing the probe.

5. The method of claim 1, wherein analyzing the data to identify neural structures at the surgical site further comprises processing the data using a deep learning algorithm to automatically identify at least one neural structure.

6. The method of claim 1, further comprising transmitting data from the probe to a computing station and communicating information about at least one identified neural structure near a tip of the probe to a user.

7. The method of claim 6, further comprising creating a two-dimensional or a three-dimensional map of the at least one identified neural structure.

8. The method of claim 1, wherein the probe has a focused forward range of 1 inch or less.

9. The method of claim 1, wherein the probe has a diameter of 10 mm or less.

10. The method of claim 1, wherein inserting the probe through the incision further comprises passing the probe through an access port at the incision.

11. The method of claim 1, further comprising registering images produced by the probe to a segmented anatomical structure of a patient image volume.

12. The method of claim 1, wherein inserting the probe through the incision further comprises manually inserting the probe through the incision.

13. The method of claim 1, wherein inserting the probe through the incision further comprises robotically assisted navigation of the probe through the incision.

14. The method of claim 1, wherein the probe includes at least one optical or electrical nerve detection technology.

* * * * *